(12) United States Patent
West

(10) Patent No.: US 8,322,345 B2
(45) Date of Patent: Dec. 4, 2012

(54) SURGICAL DRAPE AND METHOD OF USE

(76) Inventor: Tamra West, Rochester, NY (US)

( * ) Notice: Subject to any disclaimer, the term of this patent is extended or adjusted under 35 U.S.C. 154(b) by 541 days.

(21) Appl. No.: 12/684,603

(22) Filed: Jan. 8, 2010

(65) Prior Publication Data

US 2010/0175700 A1    Jul. 15, 2010

Related U.S. Application Data

(60) Provisional application No. 61/204,985, filed on Jan. 14, 2009.

(51) Int. Cl.
*A61B 19/00* (2006.01)
(52) U.S. Cl. .......................... 128/855; 128/849; 206/440
(58) Field of Classification Search .......... 128/849–855; 206/438, 440
See application file for complete search history.

(56) References Cited

U.S. PATENT DOCUMENTS

| | | | | |
|---|---|---|---|---|
| 5,379,703 A * | 1/1995 | Marshall | ......................... | 108/90 |
| 5,618,278 A | 4/1997 | Rothrum | | |
| 5,803,086 A * | 9/1998 | Scholz et al. | ................. | 128/849 |
| 6,244,268 B1 * | 6/2001 | Annett et al. | ................. | 128/849 |
| 6,476,456 B1 * | 11/2002 | Boden, Jr. | ..................... | 257/486 |
| 7,044,133 B2 * | 5/2006 | Lohrengel et al. | ............ | 128/851 |
| 7,086,409 B2 | 8/2006 | Robinson | | |
| 7,305,991 B2 * | 12/2007 | Santilli et al. | ................. | 128/849 |
| 7,610,918 B2 | 11/2009 | Bowen | | |
| 7,654,266 B2 * | 2/2010 | Corbitt, Jr. | .................... | 128/849 |
| 7,891,359 B2 * | 2/2011 | Corbitt et al. | ................. | 128/849 |
| 2005/0229937 A1 * | 10/2005 | Salvaggio et al. | ............ | 128/849 |

(Continued)

FOREIGN PATENT DOCUMENTS

WO    WO03/061505 A1    7/2003

(Continued)

OTHER PUBLICATIONS

Proxima Surgical Drapes, Gowns & Standard Packs Catalog, Proxima Underbuttocks Drape with 7" Cuff (18cm), Ref: DYNJP6001, webpage, http://www.medline.com/Literature/Proxima%20Catalog%20.pdf, p. 104, U.S., 2004.

(Continued)

*Primary Examiner* — Nicholas Lucchesi
*Assistant Examiner* — Kari Petrik
(74) *Attorney, Agent, or Firm* — Tracy Jong Law Firm; Tracy P. Jong; Cheng Ning Jong

(57) ABSTRACT

A surgical drape includes a sheet with a shoulder portion, a body portion and a pull tab. The shoulder portion is folded longitudinally in half to form a container such that the transverse edges of the container are sealed and the body portion is folded transversely in half and rolled into a tight drape roll which is disposed and removably secured within the container. In use, the container is removably attached to a surface of an operating table such that a portion of a patient can be placed upon the container. The tight drape roll and the pull tab are configured such that when a patient is placed upon the container, the tight drape roll can be easily unfurled by pulling on the pull tab to form a relatively flat drape surface. In another embodiment, a waste bag is removably disposed on the container. In yet another embodiment, a fluid collection and drainage pouch is removably disposed on and integrated into the body portion.

12 Claims, 8 Drawing Sheets

U.S. PATENT DOCUMENTS

2006/0081261 A1    4/2006  Corbitt, Jr.
2006/0219249 A1*  10/2006  Czajka et al. ................. 128/849
2008/0029102 A1    2/2008  Santilli
2008/0210246 A1*   9/2008  Johansson et al. ............ 128/851
2008/0312629 A1*  12/2008  Yasuda et al. ............ 604/385.02

FOREIGN PATENT DOCUMENTS

WO    WO03/103525 A2   12/2003

OTHER PUBLICATIONS

Proxima Surgical Drapes, Gowns & Standard Packs Catalog, Proxima Underbuttocks Drape with Pouch and Drainage Port, Ref: DYNJP6002, webpage, http://www.medline.com/Literature/Proxima%20Catalog%20.pdf, p. 102, U.S., 2004.

* cited by examiner

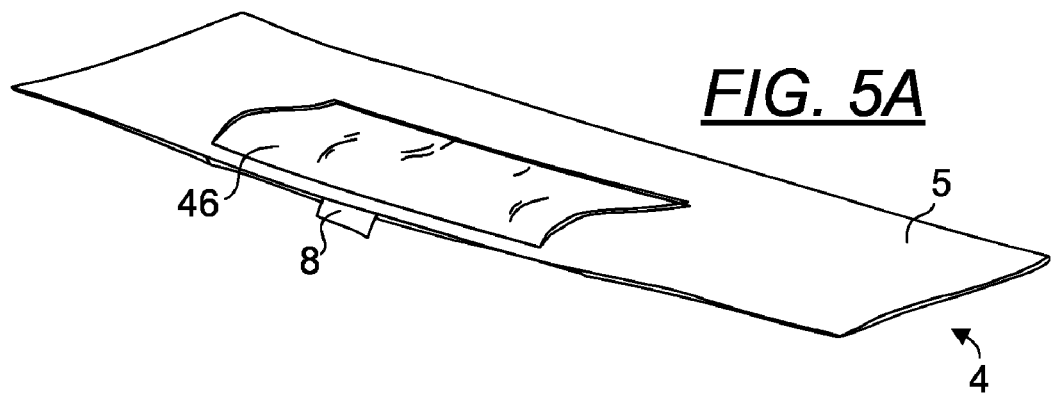
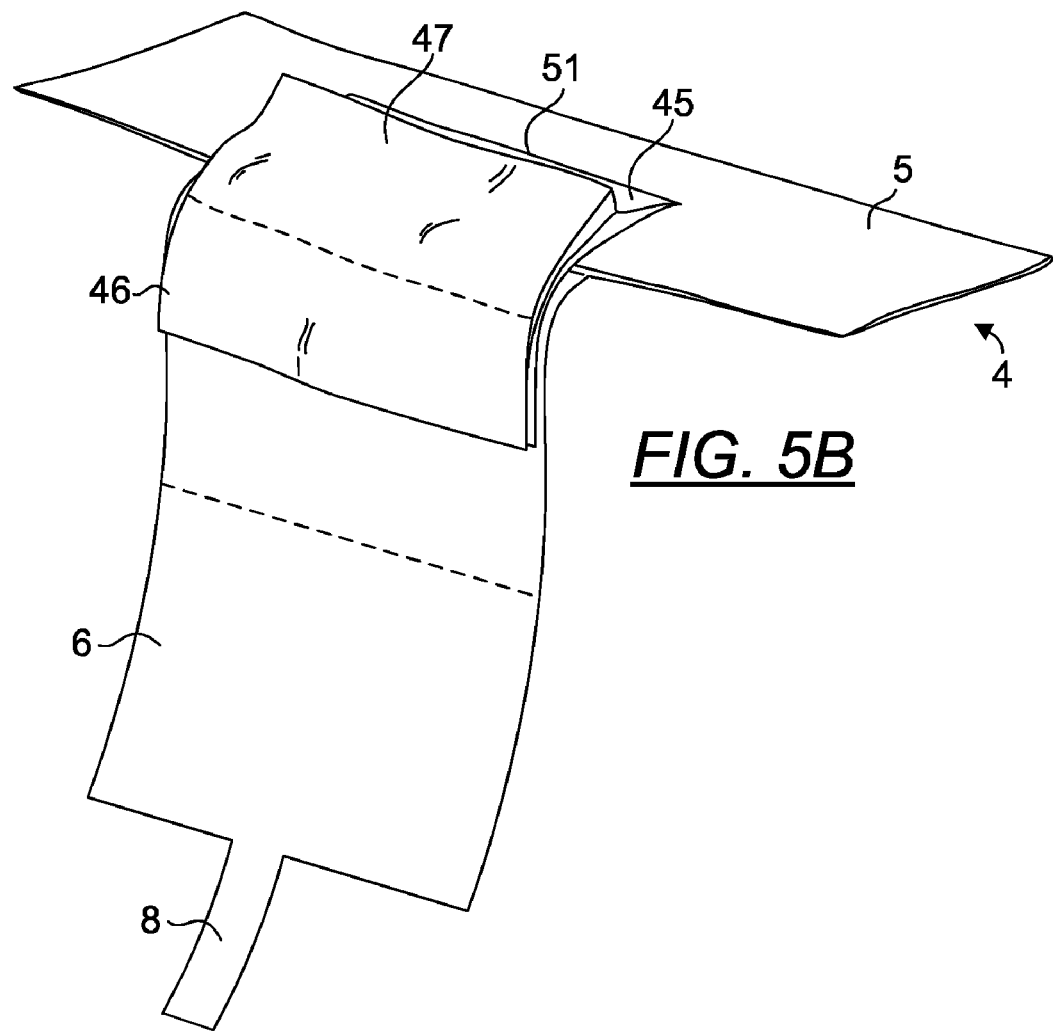

SURGICAL DRAPE AND METHOD OF USE

PRIORITY CLAIM AND RELATED APPLICATIONS

This application claims the benefit of priority from provisional application U.S. Ser. No. 61/204,985 filed on Jan. 14, 2009 in the name of Tamra S. West of Rochester, N.Y. Said application is incorporated by reference in its entirety.

BACKGROUND OF THE INVENTION

1. The Field of the Invention

The present invention is directed generally to surgical drapes, and more particularly, to underbuttock surgical drapes and surgical drapes for use in surgeries where the surgical site is located in the vicinity of an edge of an operating table.

2. Background Art

The current practice of positioning a surgical drape for underbuttock applications is a tedious multi-step process involving positioning a patient on an operating table, positioning a separate waste bag under the patient, prepping the patient, placing prepping wastes in the waste bag and discarding the bag, a surgical personnel "scrubbing in" and placing the drape between the patient's buttocks and the operating table. Prior art underbuttock drapes frequently comprise a sheet folded to form a plurality of pleats wherein one end of the sheet is positioned and secured under a patient's weight and the opposing end is pulled out to unfurl the pleats to form a substantially flat sheet.

An operating table for surgeries involving the lower body typically comes in three segments, i.e., the head segment, the leg segment and the torso segment. Currently, in preparation for a lower body surgery, the leg segment of the operating table is collapsed and a patient is positioned with his/her buttocks adjacent to the edge of the torso segment and the legs supported on stirrups. A surgical drape that is both easily removable and providing isolation between the surgical site and its surrounding must be placed near an edge of the operating table. In use, a portion of the drape covers an edge of the operating table while the remaining portion covers an area adjacent to that edge. Currently, a patient is moved to and positioned on an operating table in preparation for surgery before a surgical drape can be positioned under the patient due to the lack of an independent means to secure the drape to the operating table.

There are several drawbacks in the practice of placing a drape under a patient. Frequently, a sterile drape is unintentionally released and dropped on the floor due to its position near the edge of the operating table and the lack of an independent securing means, rendering it contaminated or otherwise unusable. In addition, it takes a longer amount of time and more effort to put a drape in place since the drape is forced under the buttocks. In use, the conventional prior art drape is not secured independently under the buttocks, thereby allowing patient maneuver or positioning of the patient to cause wrinkles in the portion of drape coming in contact with the patient. This results in wrinkle sores on the patient. Since the drape is positioned after patient has been moved to the operating table, the patient may be moved away from the edge where surgery is to be performed momentarily if difficulty is encountered in placing the drape under the patient position. This increased interaction and physical manipulation of the patient creates a higher likelihood of contamination. If a patient is put under anesthesia, adjusting the patient position becomes even more difficult.

U.S. Pat. No. 7,305,991 B2 discloses a surgical drape that is deployed from its plicated configuration. While in its plicated configuration, accidental contact between a contamination source and the pleats of the drape may render the entire drape unusable. Another disadvantage of the plicated configuration lies in the depth of pleats formed. If made too shallow, the pleats may not unfurl to result in a substantially flat drape. If made too deep, the depth of the pleats may necessitate the placement of at least a portion of the pre-deployed drape under the weight imparted by a patient, thereby complicating drape deployment. A further disadvantage of the plicated configuration lies in an improperly deployed drape where the pleats are not completely unfurled. This problem may leave folds in the drape whereby these folds can collect surgical waste or stop it from rolling down to a purpose built collecting bin. An improperly deployed drape may also deflect waste outside of the collecting bin, thereby contaminating the area outside of the collecting bin.

There exists a need for a safe under-patient surgical drape which is deployable easily and without fail.

SUMMARY OF THE INVENTION

In accordance with the present invention, there is provided a surgical drape, comprising a container, an attaching means of said container to a surface which the drape is designed to protect, and a surgical drape removably disposed inside said container. In one embodiment, the surgical drape is formed from a single sheet. In another embodiment, the surgical drape is formed from a combination of components.

In a single sheet configuration, there is provided a T-shaped fluid impervious film having a pull tab, a shoulder portion and a body portion disposed substantially at right angle to the shoulder portion and the pull tab is disposed at a free edge of the body portion. The sheet is generally made of a fluid impervious, sterile material, such as polyethylene or vinyl. The shoulder portion is configured to form a container within which the body portion and a substantial portion of the pull tab are disposed. It is common practice to place a bucket underneath and adjacent to a surgical site such that surgical waste can be guided via a drape into and collected in the bucket. In use, the shoulder portion is placed on and secured to an operating table to protect the operating table from contamination due to secretions or any surgical waste. In use, the body portion is deployed to provide extended coverage to the shoulder portion. The body portion additionally acts as a waste guiding surface to ensure proper collection of surgical waste in the bucket.

In packaging, the drape starts out as a single sheet with appropriate cutouts already made to form a shoulder portion, a body portion and a pull tab, all of which are substantially rectangular. The shoulder portion comprises a first longitudinal central axis, a first transverse central axis and a first fold line disposed collinear with the first longitudinal central axis. The shoulder portion is folded along the first fold line to form a container having a top cover. This top cover has an upper surface and a bottom cover. The bottom cover has a free edge, an upper surface and a bottom surface. The top and bottom covers are adhered together on their transverse edges. The body portion comprises a working surface, a second longitudinal central axis, a second transverse central axis and a second fold line disposed collinear with the second transverse central axis, a proximal transverse edge, and a distal transverse edge. The proximal transverse edge is connected to the free edge of the bottom cover and the second longitudinal central axis is substantially collinear with the first transverse central axis. The pull tab has a free transverse edge and a shared transverse edge wherein the shared transverse edge is connected to the distal edge of the body portion. An attaching means is longitudinally disposed on the bottom surface of the bottom cover.

Alternatively, hook and loop fasteners may be disposed on portions of the shoulder and body portions of the surgical drape to secure the drape to an operating table. The body portion is folded along the second fold line to form two overlap flaps having a folded edge and a free edge such that the working surface is substantially covered, wherein the overlap flaps are rolled beginning at the folded edge towards the free edge into a substantially tight drape roll disposed within the cavity formed within the upper and bottom covers and the free transverse edge of the pull tab is disposed at a location outside of the cavity for easy access. The tight drape roll is removably secured to the upper surface of the bottom cover with at least one securing means.

In one embodiment, the securing means comprises an adhesive tape having a tear line aligned in a direction transverse to the direction in which the tight drape roll is rolled such that a gripping force applied to the free transverse edge of the pull tab breaks the tear line, detaching the tight drape roll from the upper surface of the bottom cover, causing the tight drape roll to be unfurled. In another embodiment, the securing means comprises a drop of adhesive.

It is a primary object of the present invention to provide a surgical drape that is not easily contaminated in its pre-deployed state.

It is another object of the present invention to provide a surgical drape that is capable of being deployed easily and with high likelihood of success.

It is yet another object of the present invention to provide a surgical drape that can be positioned in place prior to positioning a patient onto it.

It is yet another object of the present invention to provide a surgical drape that can save valuable surgical time.

It is a further object of the present invention to provide a surgical drape that requires minimal surgical personnel-patient interaction.

It is a further object of the present invention to provide a surgical drape that comes with a removable integral waste bag which helps save preparation ("prep") time.

It is a further object of the present invention to provide a surgical drape that comes with a removable integral fluid collection and drainage bag which helps save prep and surgical time.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification and claims. The present invention is capable of other embodiments and of being practiced and carried out in various ways. Also it is to be understood that the phraseology and terminology employed herein are for the purpose of description and should not be regarded as limiting.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 5A is a perspective view of one embodiment of the present invention having a removable integral waste bag in its collapsed state.

FIG. 5B is a perspective view of the embodiment shown in 5A showing the removable integral waste bag in its ready-to-use state.

Figure 1:
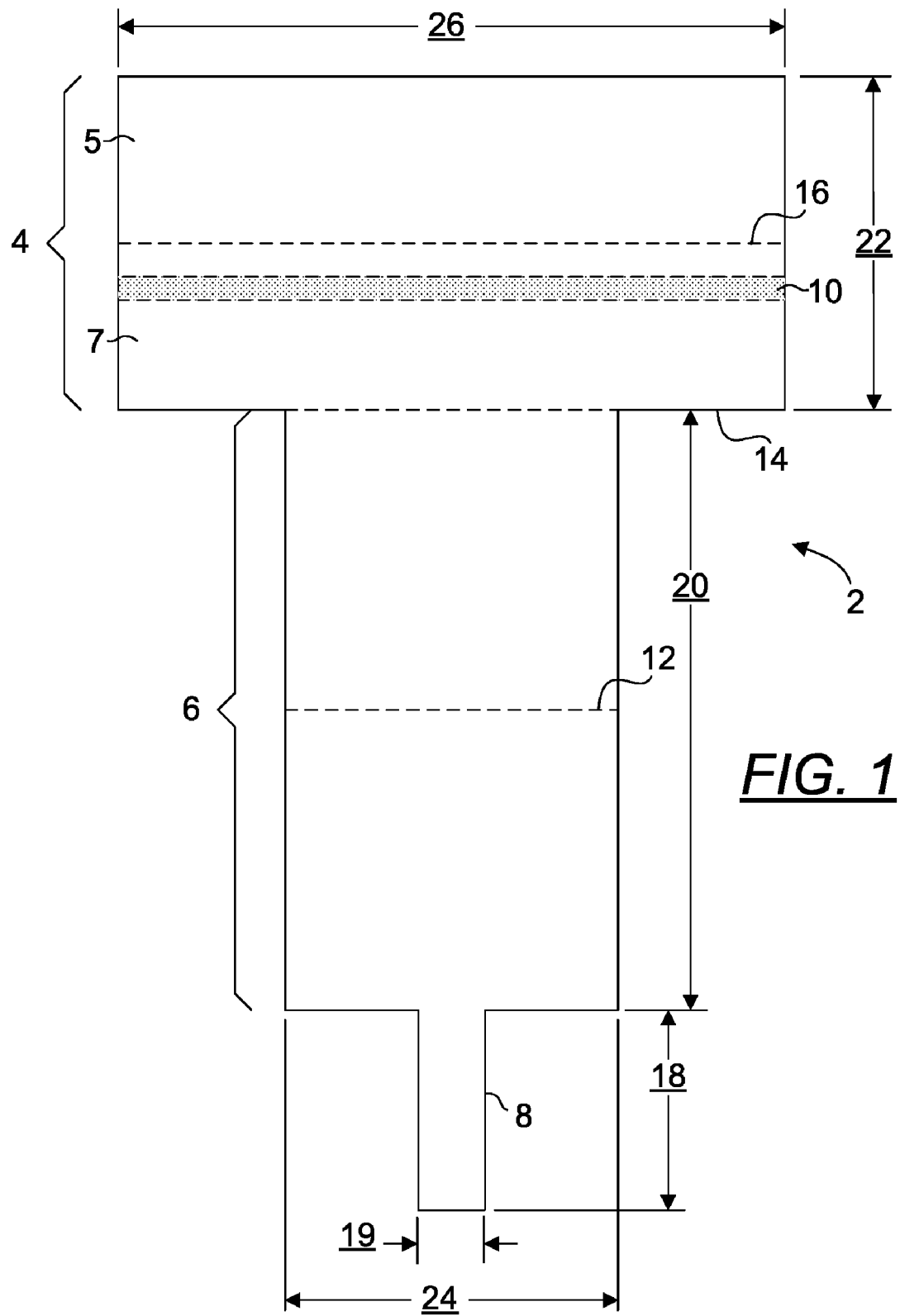
FIG. 1 is a top orthogonal view of one embodiment of the present surgical drape in its spread-out state.

The drawings are not to scale, in fact, some aspects have been emphasized for a better illustration and understanding of the written description.

PARTS LIST

2—surgical drape
3—prior art surgical drape
4—shoulder portion of drape
5—top cover of container
5a,b—transverse edges of top cover of container
6—body portion of drape
6a—proximal portion of body portion
6b—distal portion of body portion
6c—tight drape roll
7—bottom cover of container
7a,b—transverse edges of bottom cover of container
8—pull tab
8a—free transverse edge of pull tab
10—drape securing means
12—second fold line
14—mouth of drape container
16—first fold line
18—length of pull tab
19—width of pull tab
20—length of drape body
22—width of drape shoulder
24—width of drape body
26—length of drape shoulder
27—operating table
28—torso segment of operating table 30—leg segment of operating table
32—head segment of operating table
34—surgical waste bucket
36—patient
38—operating table edge where surgical site is located
40—drape body roll direction
42—surgical-personnel attempting to position drape under patient's buttocks
43—tape securing tight body portion to bottom cover
44—tear line on tape 43
45—one side of waste bag
46—waste bag
47—opposing side of waste bag
48—fluid collection and drainage pouch
48a—front lip of fluid collection and drainage pouch
48b—rear lip of fluid collection and drainage pouch
49—drainage port
50—large fluid collection and drainage pouch
52—fold line on front portion of fluid collection and drainage pouch
54—fold line on rear portion of fluid collection and drainage pouch
55—drainage port
56—front portion of fluid collection and drainage pouch
58—rear portion of fluid collection and drainage pouch
60—front lip of fluid collection and drainage pouch

PARTICULAR ADVANTAGES OF THE INVENTION

The present invention provides a surgical drape that simplifies the steps required to prep a surgical patient, minimizes the exposure of the working surface of the surgical drape surface in storage and during prepping of a surgical patient, reduces the likelihood of a drape being accidentally dropped and contaminated, and reduces the amount of personnel-patient interaction in setting up a drape.

The novel practice of positioning a surgical drape for underbuttock applications comprises the step of positioning and securing the drape onto an operating table, the step of positioning a patient on a portion of the drape, the step of erecting a removable integral waste bag adjacent to the patient, the step of prepping the patient, the step of placing prepping waste in the removable integral waste bag, removing and discarding the waste bag, the step of deploying the drape by pulling on the pull tab. With the present novel drape, the act of deploying the drape can be performed by any personnel since it requires no direct interaction between the personnel with the patient.

In contrast to prior art practice, the step of positioning a patient after setting up a drape simplifies the process of inserting a sheet between the patient and the operating table. This step further eliminates the need to adjust the position of a patient in order to place the drape, thereby reducing the level and amount of personnel-patient interactions. This step further reduces the possibility of developing wrinkles in the drape which may cause wrinkle sores in the patient.

A removable integral waste bag is provided to remove the need to search for a separate waste bag to contain the waste generated during patient prepping. None of the prior art discloses an underbuttocks surgical drape having an integral waste bag.

The novel packaging of the drape provides protection for the drape while in storage, maintains drape sterility and provides easy deployment of the drape. The drape is folded in half and rolled into a tight drape roll for storage. Such arrangement minimizes the exposure of the personnel or patient-facing surface to the environment. Such arrangement also provides protection against accidental spillage of waste on the drape. In addition, such arrangement eliminates the difficulty of deploying a drape by offsetting the tight drape roll from the drape portion upon which a patient is placed. In contrast to prior art drapes, the current invention provides a drape that is protected in its entirety while its container is disposed on an operating table prior to the deployment of the drape.

For a drape embodiment comprising a removable integral fluid collection and drainage pouch, fluid collecting activity can be started immediately once the drape has been deployed. There is no need to search for a separate fluid collection and drainage pouch, thereby saving valuable surgical time. In contrast to the prior art pouch-like container disclosed in U.S. Pat. No. 7,305,991 B2, the current invention discloses a fluid collection and drainage pouch that is protected in its entirety while its container is disposed on an operating table prior to the deployment of the drape.

DETAILED DESCRIPTION OF A PREFERRED EMBODIMENT

FIG. 1 is a top orthogonal view of one embodiment of the present surgical drape 2 in its spread-out state. The surgical drape 2 comprises a shoulder portion 4, a body portion 6 and a pull tab 8. The shoulder portion 4 has a length 26 and a width 22. A first fold line 16 is shown disposed at substantially in the middle of the width 22 of the shoulder portion 4 dividing the shoulder portion 4 into a top cover 5 and a bottom cover 7. The body portion 6 has a length 20 and a width 24. A second fold line 12 is shown disposed at substantially in the middle of the length 20 of the body portion 6. The width 24 of body portion 6 is centered substantially along the length 26 of the shoulder portion 4. The width 19 of pull tab 8 is centered substantially along the width 24 of the body portion 6. A double sided adhesive tape 10 is disposed on the bottom surface of the bottom cover portion 7. Referring to FIG. 1, the relative position of the tape is shown on the top surface of the bottom cover portion 7. In one embodiment, the surgical drape 2 is constructed from polyethylene. In another embodiment, the surgical drape 2 is constructed from vinyl. In yet another embodiment, the surgical drape 2 is constructed from a material sufficiently thin, flexible and impervious to fluids.

Figure 2:
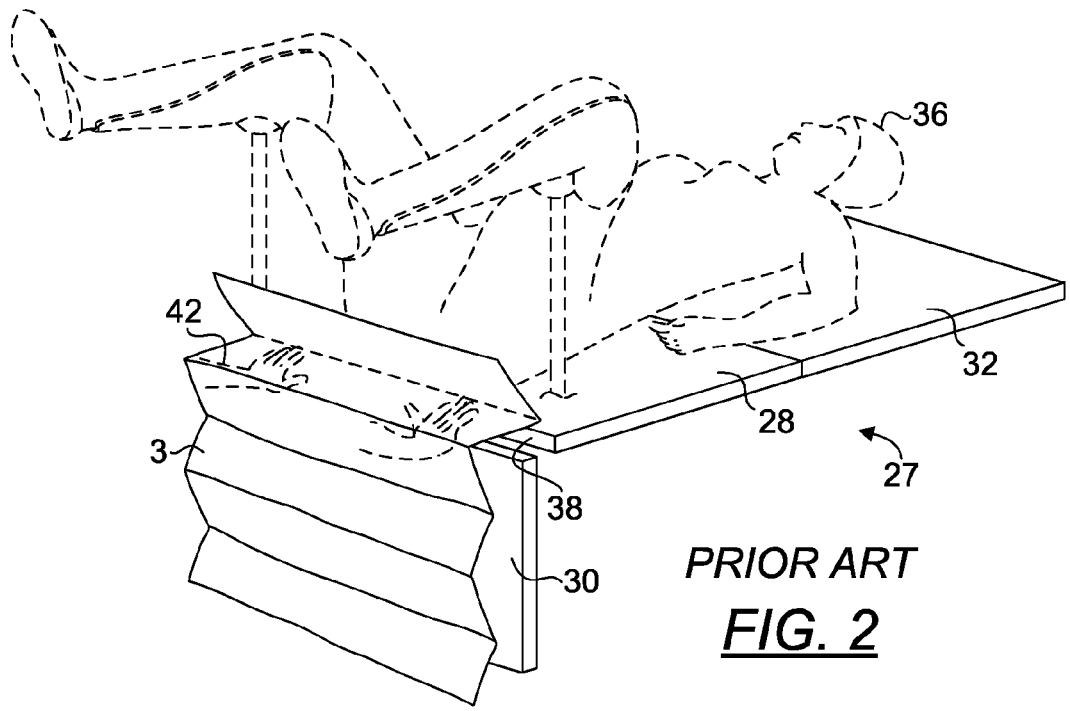
FIG. 2 is a perspective view of a prior art surgical drape being positioned under a patient's buttocks.

FIG. 2 is a perspective view of a prior art surgical drape being positioned under a patient's buttocks. A patient 36 positioned in the femoral position is placed on an operating table. The torso of the patient 36 is laid flat on the operating table with the head and torso segments 32, 28 of the operating table 27 positioned flat and the leg segment 30 of the operating table lowered. The present invention is also applicable to a patient placed in the lithotomy position or a surgical site located at an edge of an operating table. In this example, the patient is positioned at edge 38 of the torso segment 28 of the operating table 27. In prior art practice as illustrated in FIG. 2, a patient 36 is first positioned on an operating table 27. A surgical drape 3 is then forced in between the patient 36 and the operating table 27. The prior art drape is a drape material folded into a plurality of pleats and stored prior to use. In use, the pleats are unfurled to form a relatively flat drape. Referring to FIG. 2, during surgical prep, a surgical personnel 42 places a drape under the buttocks area to protect the operating table 27 from surgical contamination.

Figure 3:
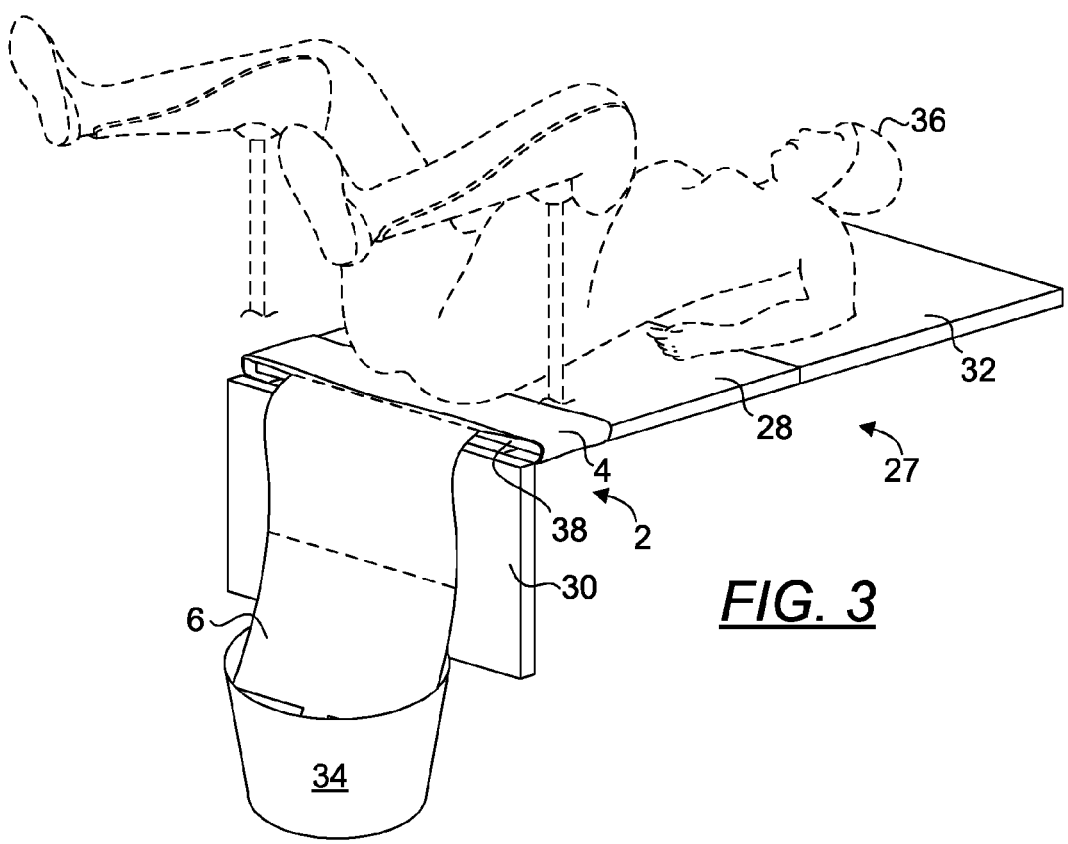
FIG. 3 is a perspective view of one embodiment of the present invention in use and fully deployed.

FIG. 3 is a perspective view of one embodiment of the present invention in use and fully deployed. The novel drape of the present invention 2 is positioned at an edge 38 of an operating table 27 on which surgery is performed. A double sided tape (not shown) is disposed on the bottom surface of the bottom cover 7 to secure the shoulder portion 4 to a surface of the operating table 27. Referring to FIGS. 1 and 3, the length 26 of the shoulder portion 4 is sized such that its transverse edges can be tucked under edges of the operating table 27 to further secure the surgical drape 2 while being positioned in place on the operating table 27. In use, the body portion 6 of the surgical drape 2 is led into and positioned in a surgical waste collection bucket 34.

Figure 3A:
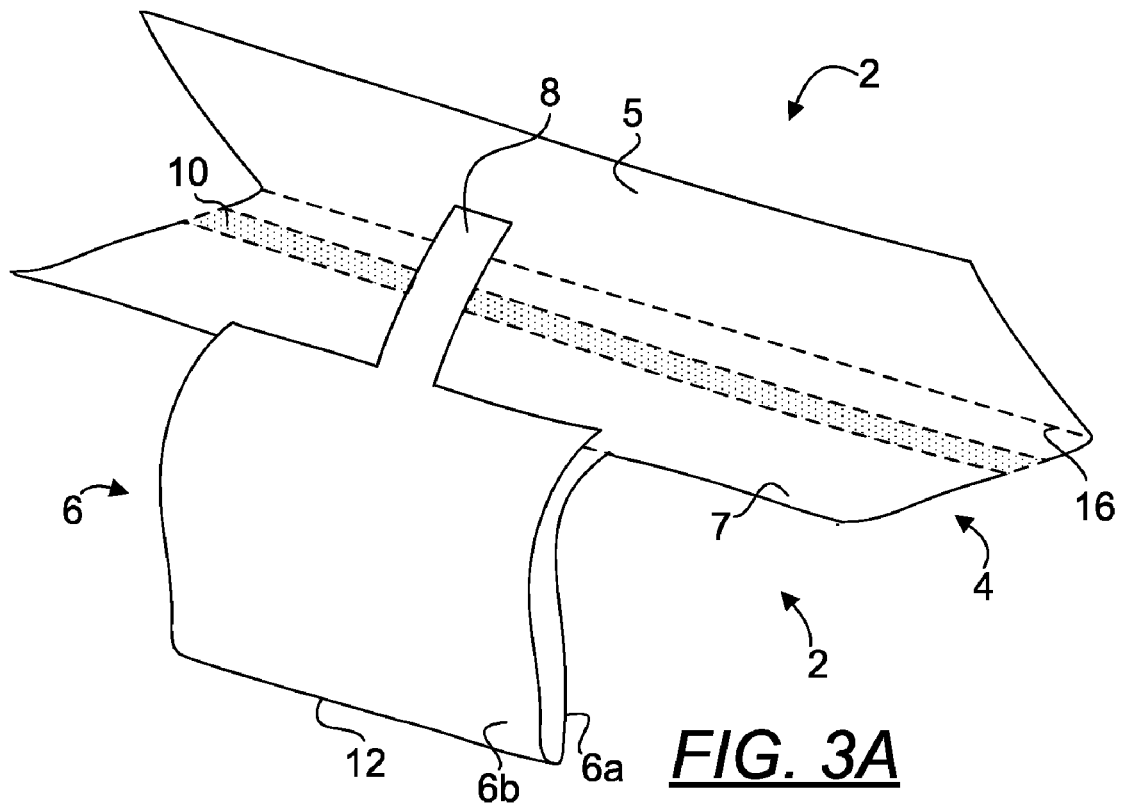
FIG. 3A-3C are perspective views of one embodiment of the present invention illustrating the novel steps by which the drape is packaged.
Figure 3B:
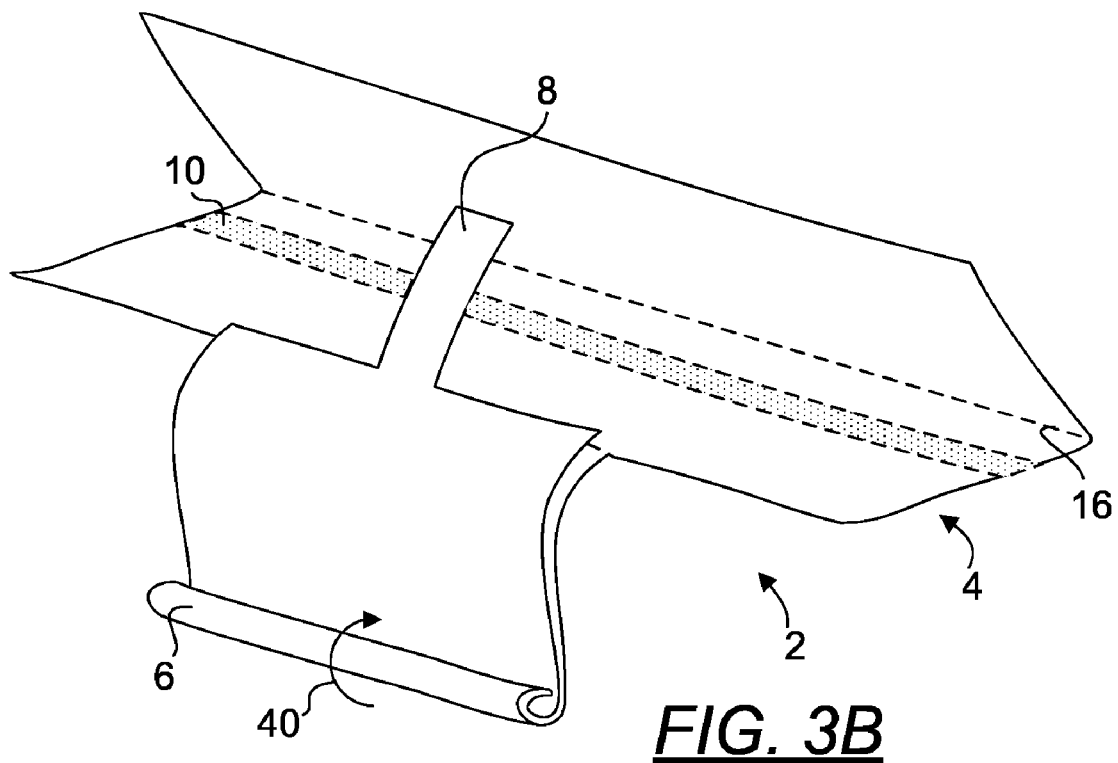
Figure 3C:
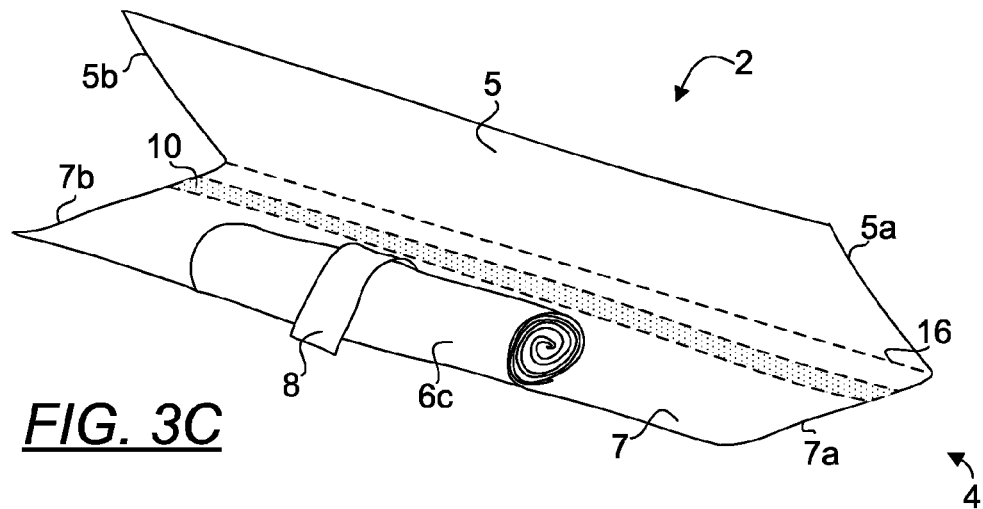

FIG. 3A-3C are perspective views of one embodiment of the present invention illustrating the novel steps by which the drape is packaged. FIG. 3A shows the shoulder portion 4 of the present surgical drape 2 folded in half along the first fold line 16 to form a top cover 5 and a bottom cover 7. FIG. 3A further shows the body portion 6 of the present surgical drape 2 folded in half along second fold line 12 to form a proximal portion 6a and a distal portion 6b. FIG. 3B shows the folded body portion 6 of FIG. 3A getting rolled in direction 40 starting from the folded edge defined by second fold line 12. FIG. 3C shows a tight drape roll 6c disposed on the bottom cover 7 of the shoulder portion 4 as a result of rolling the folded body portion 6. In order to complete the construction of the shoulder portion 4, the transverse edges 5a, 5b of the top cover 5 are secured to the transverse edges 7a, 7b of the bottom cover 7 via a securing means. Once the transverse edges 5a, 5b, 7a, 7b of the top and bottom covers 5, 7 are secured, a container is therefore formed to provide protection to the tight drape roll 6c within its cavity. The tight drape roll 6c is further removably secured to the bottom cover 7 of the shoulder portion via a securing means (not shown). In one embodiment, the securing means is an adhesive tape having a tear line positioned such that the tight drape roll 6c can be separated from the bottom cover 7 once a separation force is applied without undue effort. In another embodiment, the securing means is a drop of adhesive between the tight drape roll 6c and the bottom cover 7. Referring to FIG. 1 and FIG. 3C, the length 18 of pull tab 8 is configured such that when a tight drape roll 6c is formed of the body portion 6, the free edge of the pull tab 8 protrudes outside of the container formed of the shoulder portion 4 for easy access. In one embodiment, an absorbent layer is provided only on the upper surface of the top cover. In another embodiment, a second absorbent layer is provided on the bottom surface of the bottom cover.

Figure 3D:
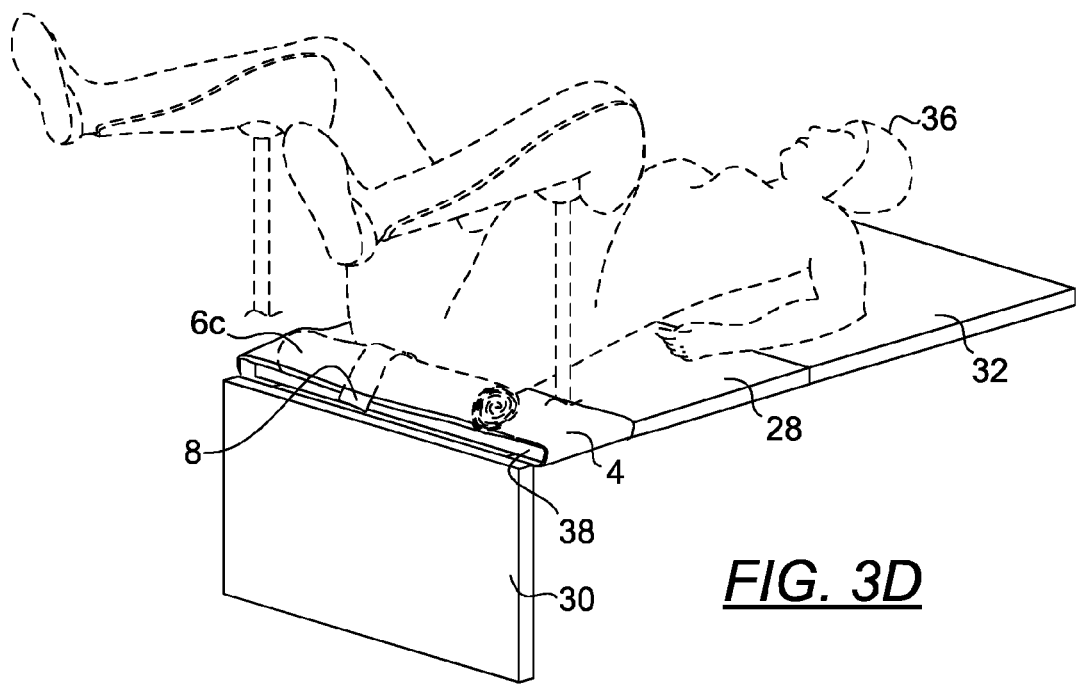
FIG. 3D is a perspective view of one embodiment of the present invention illustrating the relative position of an undeployed drape with respect to the placement of a patient.

FIG. 3D is a perspective view of one embodiment of the present invention illustrating the relative position of a pre-deployed drape with respect to the placement of a patient 36. For clarity, the tight drape roll 6c is shown in broken lines and positioned at an offset from the portion of the shoulder portion 4 upon which the patient 36 is positioned.

Figure 4:
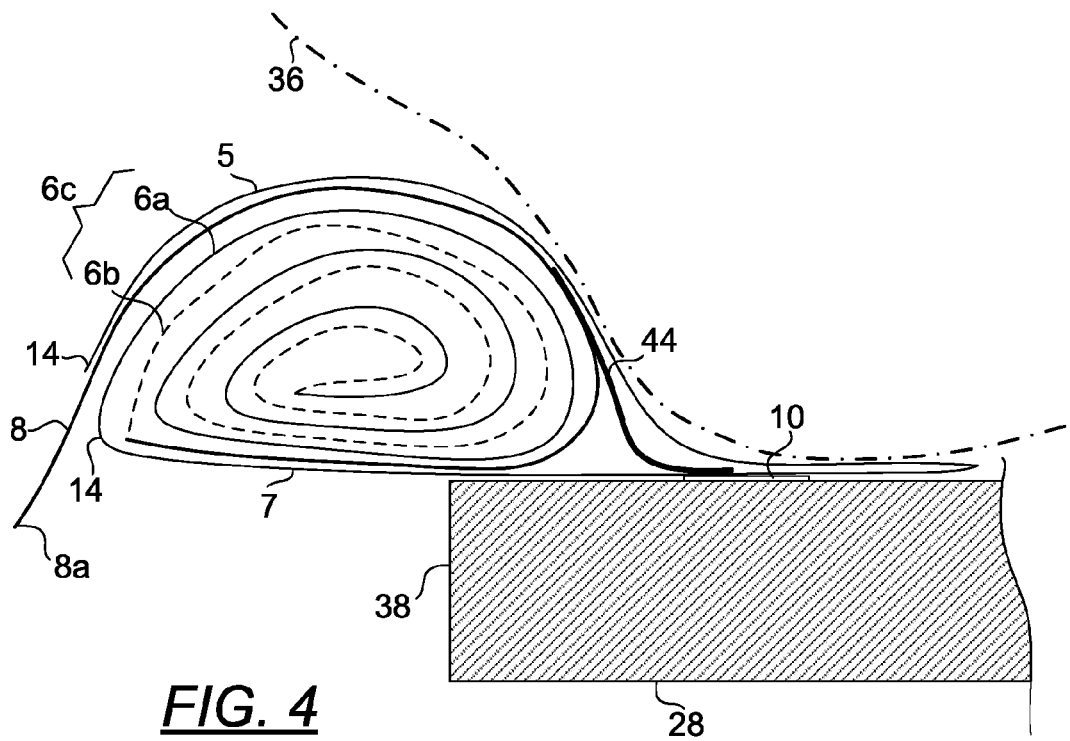
FIG. 4 is a side orthogonal cross-sectional view of one embodiment of the present invention in use.

FIG. 4 is a side orthogonal cross-sectional view of one embodiment of the present invention in use. The tight drape roll 6c is enlarged to show its rolled configuration, the relationship of the pull tab 8 to the tight drape roll 6c and the relative position of the tight drape roll 6c with respect to the placement of a patient 36. In this view, the proximal portion 6a is shown as a solid line while the distal portion 6b is shown as a broken line. In use, the tight drape roll 6c is positioned at an offset from the portion of the shoulder portion 4 upon which the patient 36 is positioned. In the tight drape roll 6c configuration, the free transverse edge 8a of the pull tab 8 is disposed via an opening 14, outside of the container defined by the top and bottom covers 5, 7. A double sided tape 10 is shown securing the bottom surface of the bottom cover 7 to a surface near an edge 38 of the torso segment 28 of the operating table. In the embodiment shown, an adhesive tape 44 is used to secure the tight drape roll 6c to the upper surface of the bottom cover 7.

Figure 4A:
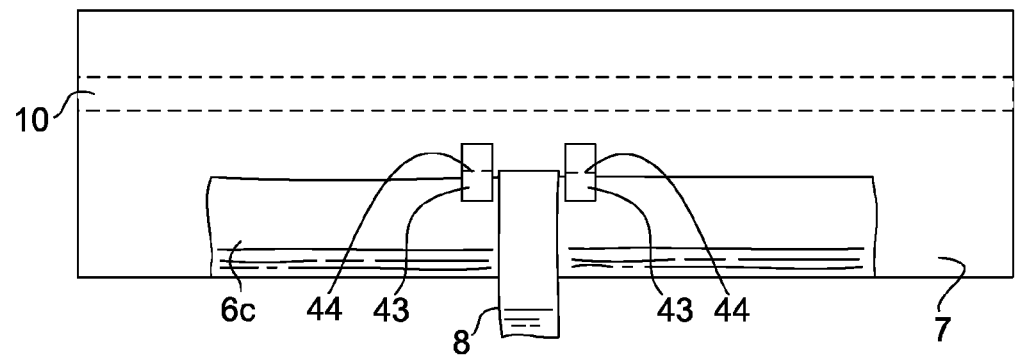
FIG. 4A is a top orthogonal view of one embodiment of the present invention illustrating the means by which the tight drape roll is secured to the upper surface of the bottom cover.

FIG. 4A is a top orthogonal view of one embodiment of the present invention illustrating the means by which the tight drape roll 6c is secured to the upper surface of the bottom cover 7 of the shoulder portion 4. In this view, the shoulder portion 4 is shown with the top cover 5 removed for clarity. In this embodiment, there are provided two adhesive tapes 43 having a tear line 44 disposed at right angle to the direction at which a force is applied to the pull tab to unfurl the tight drape roll 6c, each of which is disposed adjacent to the pull tab 8.

FIG. 5A is a perspective view of one embodiment of the present invention having a removable integral waste bag in its collapsed state. A waste bag 46 is removably attached to the upper surface of top cover 5 of the shoulder portion 4. In one embodiment, the waste bag 46 is removably secured to the upper surface of top cover 5 by means of at least one drop of adhesive. In another embodiment, the waste bag 46 is removably secured to the upper surface of top cover 5 by means of at least one adhesive tape having a tear line disposed at right angle to the direction of waste bag 46 removal. The waste bag 46 is provided to facilitate the disposal of surgical prepping waste. Once surgical prepping is completed, the waste bag 46 is detached from the top cover 5 by applying a gripping force to the waste bag 46 such that the tear line breaks, causing the waste bag 46 to break free from the top cover 5 and discarded.

FIG. 5B is a perspective view of the embodiment shown in 5A illustrating the removable integral waste bag in its ready-to-use state. As shown, the waste bag 46 is removably attached on one side 45 to the upper surface of top cover 5 such that the waste bag 46 can be opened by lifting an opposing side 47 of the waste bag 46.

Figure 6:
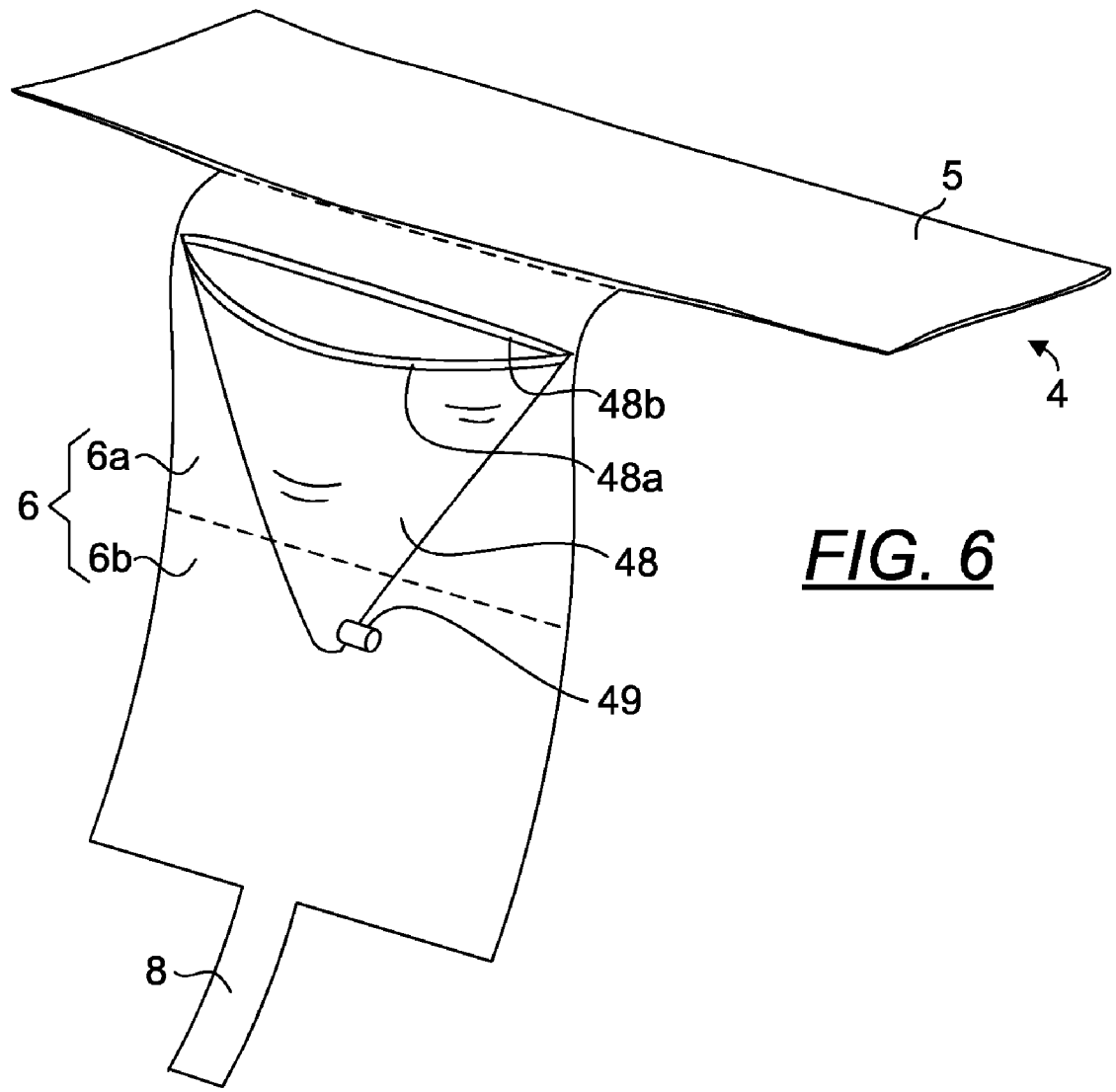
FIG. 6 is a perspective view of one embodiment of the present invention having a removable integral fluid collection and drainage pouch in its ready to use state.

FIG. 6 is a perspective view of one embodiment of the present invention having a removable integral fluid collection and drainage pouch in its ready to use state. In this embodiment, a fluid collection and drainage pouch 48 is removably attached to the proximal and distal portions 6a, 6b of the body portion 6. In another embodiment not shown, a fluid collection and drainage pouch 48 is removably attached to only the proximal portion 6a of the body portion 6. In yet another embodiment not shown, a fluid collection and drainage pouch 48 is removably attached to only the distal portion 6b of the body portion 6. The fluid collection and drainage pouch 48 is made of two generally triangular, fluid impervious sheets sealed on two edges leaving an opening facing up when deployed. A drainage port 49 is provided at the bottom of the fluid collection and drainage pouch making selective drainage of any fluids collected in the pouch possible. The opening has a front lip 48a and a rear lip 48b, wherein at least the front lip 48a is strengthened with a reinforcement strip, causing the opening to remain open once it has been propped open. In another embodiment, both front and rear lips 48a, 48b are strengthened with reinforcement strips.

Figure 7:
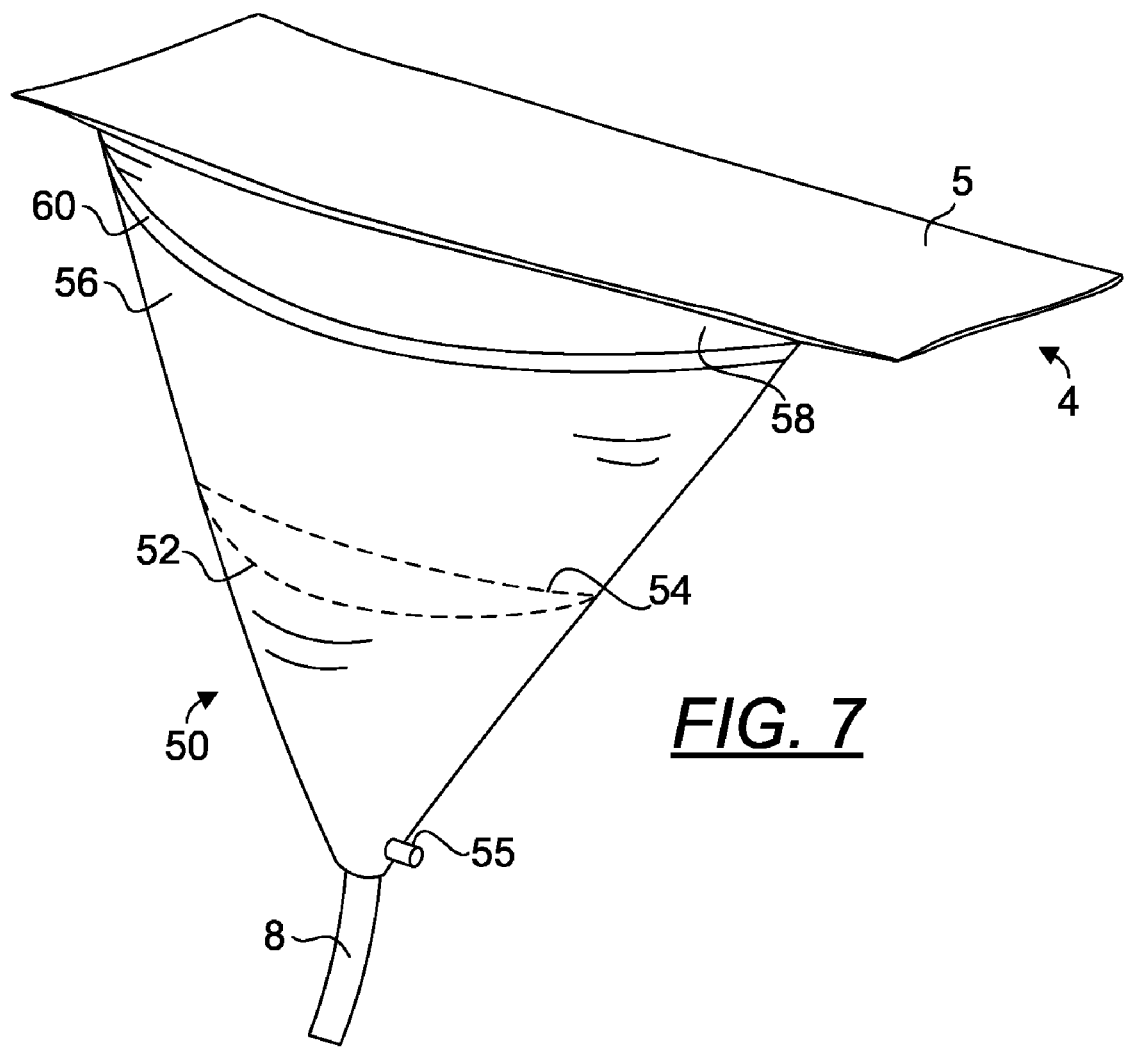
FIG. 7 is a perspective view of one embodiment of the present invention wherein the drape is also used as a fluid collection and drainage pouch.

FIG. 7 is a perspective view of one embodiment of the present invention, wherein the body portion 6 of FIG. 3 is made in the form of a fluid collection and drainage pouch 50. The shoulder portion 4 and the pull tab 8 of this embodiment are substantially similar to the respective components shown in FIG. 3. In this embodiment, a fluid collection and drainage pouch 50 is used in place of a body portion 6 as shown in FIG. 3. The fluid collection and drainage pouch 50 is made of two generally triangular, fluid impervious sheets 56, 58 sealed on two edges leaving an opening facing up when deployed. A drainage port 55 is provided at the bottom of the fluid collection and drainage pouch 50, making selective drainage of any fluids collected in the bag possible. The opening has a front lip

60 strengthened with a reinforcement strip, causing the opening to remain open once it has been propped open. The fluid collection and drainage pouch 50 is packaged much like the way the body portion 6 of FIG. 3 is packaged. The fluid collection and drainage pouch is folded in half at fold lines 52, 54 to form a folded edge, wherein the fluid collection and drainage pouch is further rolled from the folded edge towards the shoulder portion 4 to form a tight pouch roll which is placed and secured within the cavity formed of the shoulder portion. The pull tab 8 is likewise positioned such that it is easily accessible for pouch deployment.

The invention claimed is:

1. A surgical drape comprising:
    a T-shaped fluid impervious film having a shoulder portion, a pull tab and a body portion disposed substantially at right angle to said shoulder portion, wherein
    said shoulder portion has a first longitudinal central axis, a first transverse central axis and a first fold line disposed collinear with said first longitudinal central axis;
    said shoulder portion is folded along said first fold line to form a container having a top cover and a bottom cover, wherein said top cover comprises an upper surface and said bottom cover comprises a free edge, an upper surface and a bottom surface, and said top and bottom covers are adhered together at their transverse edges;
    said bottom surface of said bottom cover comprises an attaching means;
    said body portion has a working surface that is minimized in its packaged form, a second longitudinal central axis, a second transverse central axis and a second fold line disposed collinear with said second transverse central axis of said body portion, a proximal transverse edge and a distal transverse edge, wherein said proximal transverse edge is connected to said free edge of said bottom cover and said second longitudinal central axis is substantially collinear with said first transverse central axis; and
    said pull tab has a free transverse edge and a shared transverse edge, wherein said shared transverse edge is connected to said distal transverse edge of said body portion.

2. The surgical drape of claim 1, wherein said body portion is folded along said second fold line to form overlap flaps having a folded edge, wherein said overlap flaps are rolled beginning at said folded edge towards said free edge of said bottom cover into a tight drape roll thereby minimizing exposure of the working surface of said body portion to its surroundings, whereby said tight drape roll is disposed within said container and removably secured to said upper surface of said bottom cover with at least one securing means and said free transverse edge of said pull tab is disposed at a location outside of said container for easy access.

3. The surgical drape of claim 1, wherein said attaching means of said bottom cover is a double sided tape.

4. The surgical drape of claim 1, wherein said shoulder and body portions are secured by means of hook and loop fasteners.

5. The surgical drape of claim 2, wherein said tight drape roll is removably secured to said upper surface of said bottom cover by means of at least one adhesive tape having a tear line aligned in a direction transverse to the direction in which the tight drape roll is rolled, such that a gripping force applied to said free transverse edge of said pull tab breaks the tear line, causing the tight drape roll to be detached from said upper surface of said bottom cover and unfurled.

6. The surgical drape of claim 2, wherein said tight drape roll is removably secured to said upper surface of said bottom cover by means of at least one drop of an adhesive, such that a gripping force applied to said free transverse edge of said pull tab detaches said tight drape roll from said upper surface of said bottom cover, causing said tight drape roll to be unfurled.

7. The surgical drape of claim 1, further comprising a removable integral waste bag.

8. The surgical drape of claim 7, wherein said removable integral waste bag is disposed on said upper surface of said top cover by means of an adhesive tape having a tear line, whereby when a gripping force is applied to and in a direction away from said removable integral waste bag, it is separated from said top cover.

9. The surgical drape of claim 1, further comprising a removable integral fluid collection and drainage pouch removably attached to said body portion, whereby when said body portion is rolled into a tight drape roll, said fluid collection and drainage pouch is protected in its entirety and when said body portion is unfurled, said fluid collection and drainage pouch is deployed.

10. The surgical drape of claim 1, wherein said shoulder and body portions are made of a material selected from the group consisting of polyethylene and vinyl.

11. The surgical drape of claim 1, wherein said upper surface of said top cover is protected by an absorbent layer.

12. The surgical drape of claim 11, wherein said bottom surface of said bottom cover is protected by a second absorbent layer.

\* \* \* \* \*